US012655331B2

(12) United States Patent
Negele et al.

(10) Patent No.: US 12,655,331 B2
(45) Date of Patent: Jun. 16, 2026

(54) DRY ELECTRODE ADHESIVE

(71) Applicant: Henkel AG & Co. KGaA, Duesseldorf (DE)

(72) Inventors: Carla Negele, Neuss (DE); Inge van der Meulen, Eersel (NL); Stijn Gillissen, Hasselt (BE); Tobias Roschek, Solingen (DE); Frank Goethel, Chemnitz (DE); Alissa Besler, Duesseldorf (DE); Anja Schneider, Duesseldorf (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 985 days.

(21) Appl. No.: 17/446,476

(22) Filed: Aug. 31, 2021

(65) Prior Publication Data

US 2022/0098454 A1 Mar. 31, 2022

Related U.S. Application Data

(63) Continuation of application No. PCT/EP2020/055388, filed on Mar. 2, 2020.

(30) Foreign Application Priority Data

Mar. 7, 2019 (EP) ..................................... 19161196

(51) Int. Cl.
C09J 133/12 (2006.01)
A61B 5/259 (2021.01)
(Continued)

(52) U.S. Cl.
CPC ............. *C09J 133/12* (2013.01); *A61B 5/259* (2021.01); *A61B 5/28* (2021.01); *C09J 7/385* (2018.01); *C09J 9/02* (2013.01); *G01N 33/4833* (2013.01)

(58) Field of Classification Search
CPC ... C09J 133/12; C09J 7/385; C09J 9/02; C09J 133/066; G01N 33/4833; A61B 5/259; (Continued)

(56) References Cited

U.S. PATENT DOCUMENTS 4,524,087 A 6/1985 Engel
4,640,289 A 2/1987 Craighead
(Continued)

FOREIGN PATENT DOCUMENTS

CA 1203286 A 4/1986
CA 2379268 A1 9/2003
(Continued)

OTHER PUBLICATIONS

International Search Report for PCT/EP2020/055388 mailed Mar. 27, 2020.
(Continued)

*Primary Examiner* — Scott R. Walshon
(74) *Attorney, Agent, or Firm* — Mary K. Cameron

(57) ABSTRACT

The present invention relates to an ionically conductive pressure sensitive adhesive composition useful as an electrode adhesive, which is an ionically conductive (meth) acrylate based pressure sensitive adhesive allowing prolonged biosignal monitoring times without skin irritation and loss of signal quality.

19 Claims, 9 Drawing Sheets

(51) Int. Cl.

| | |
|---|---|
| *A61B 5/28* | (2021.01) |
| *C09J 7/38* | (2018.01) |
| *C09J 9/02* | (2006.01) |
| *G01N 33/483* | (2006.01) |

(58) Field of Classification Search

CPC .... A61B 5/276; A61B 5/291; A61B 2562/125

See application file for complete search history.

(56) References Cited

U.S. PATENT DOCUMENTS

| | | | |
|---|---|---|---|
| 4,926,878 | A | 5/1990 | Snedeker |
| 4,962,878 | A | 10/1990 | Kent |
| 5,082,595 | A | 1/1992 | Glackin |
| 5,205,297 | A | 4/1993 | Montecalvo et al. |
| 5,218,973 | A | 6/1993 | Weaver et al. |
| 5,378,405 | A | 1/1995 | Gutman et al. |
| 5,385,679 | A | 1/1995 | Uy et al. |
| 5,496,363 | A | 3/1996 | Burgio et al. |
| 5,686,516 | A | 11/1997 | Tzur |
| 5,797,517 | A | 8/1998 | Weinstein |
| 5,800,685 | A | 9/1998 | Perrault |
| 5,848,966 | A | 12/1998 | Gusakov et al. |
| 6,121,508 | A | 9/2000 | Bischof et al. |
| 6,668,380 | B2 | 12/2003 | Marmaropoulos et al. |
| 6,717,057 | B1 | 4/2004 | Segall et al. |
| 7,842,742 | B2 | 11/2010 | Amano et al. |
| 7,955,512 | B2 | 6/2011 | Park et al. |
| 8,404,344 | B2 | 3/2013 | Ukei et al. |
| 8,673,184 | B2 | 3/2014 | Burnham et al. |
| 9,697,954 | B2 | 7/2017 | Nomura et al. |
| 2003/0222573 | A1 | 12/2003 | Mcdonough et al. |
| 2005/0003167 | A1 | 1/2005 | Kitch et al. |
| 2005/0197450 | A1 | 9/2005 | Amano et al. |
| 2005/0266238 | A1 | 12/2005 | Amano et al. |
| 2006/0024494 | A1 | 2/2006 | Amano et al. |
| 2007/0293751 | A1 | 12/2007 | Axelgaard et al. |
| 2008/0131488 | A1 | 6/2008 | Kawamura et al. |
| 2008/0178929 | A1 | 7/2008 | Skov et al. |
| 2009/0163626 | A1 | 6/2009 | Ukei et al. |
| 2010/0016702 | A1 | 1/2010 | Greene et al. |
| 2011/0104376 | A1 | 5/2011 | Bielek et al. |
| 2011/0136009 | A1 | 6/2011 | Muthu et al. |
| 2012/0041296 | A1 | 2/2012 | Garstka et al. |
| 2013/0123451 | A1 | 5/2013 | Takeda et al. |
| 2013/0164478 | A1 | 6/2013 | Yamamoto et al. |
| 2013/0172724 | A1 | 7/2013 | Ali Mohamed Aziz et al. |
| 2014/0041296 | A1 | 2/2014 | Ichihashi et al. |
| 2014/0079949 | A1 | 3/2014 | Hanaki et al. |
| 2014/0262446 | A1 | 9/2014 | Burnham et al. |
| 2014/0295180 | A1 | 10/2014 | Yamagata et al. |
| 2017/0299542 | A1 | 10/2017 | Amouzadeh et al. |
| 2017/0323698 | A1 | 11/2017 | Hatakeyama et al. |
| 2018/0072930 | A1 | 3/2018 | Hatakeyama et al. |
| 2018/0085019 | A1 | 3/2018 | Hatakeyama et al. |
| 2018/0086948 | A1 | 3/2018 | Hatakeyama et al. |
| 2018/0229023 | A1 | 8/2018 | Hatakeyama et al. |
| 2018/0334596 | A1 | 11/2018 | Lutz et al. |
| 2019/0048193 | A1* | 2/2019 | Naier ................... C09D 139/04 |
| 2019/0298661 | A1 | 10/2019 | Murnane et al. |
| 2019/0338167 | A1* | 11/2019 | Fujita .................... C09J 139/04 |

FOREIGN PATENT DOCUMENTS

| | | | |
|---|---|---|---|
| CN | 103827237 | A | 5/2014 |
| CN | 105455804 | A | 4/2016 |
| DE | 2935238 | A1 | 3/1981 |
| DE | 10254703 | A1 | 6/2004 |
| EP | 0322098 | A1 | 6/1989 |
| EP | 1693430 | A2 | 8/2006 |
| EP | 3211033 | A1 | 8/2017 |
| EP | 3360473 | A1 | 8/2018 |
| JP | H0195962 | A | 4/1989 |
| JP | 2003138240 | A | 5/2003 |
| JP | 2005213455 | A | 8/2005 |
| JP | 2006045475 | A | 2/2006 |
| JP | 2006152154 | A | 6/2006 |
| JP | 2007070400 | A | 3/2007 |
| JP | 2007084632 | A | 4/2007 |
| JP | 2007191532 | A | 8/2007 |
| JP | 2009193682 | A | 8/2009 |
| JP | 2010037355 | A | 2/2010 |
| JP | 2012001737 | A | 1/2012 |
| JP | 2013221093 | A | 10/2013 |
| WO | 8102097 | A1 | 8/1981 |
| WO | 9309713 | A1 | 5/1993 |
| WO | 9522370 | A1 | 8/1995 |
| WO | 9724149 | A1 | 7/1997 |
| WO | 0045698 | A1 | 8/2000 |
| WO | 0075255 | A2 | 12/2000 |
| WO | 2001048111 | A1 | 7/2001 |
| WO | 03087250 | A1 | 10/2003 |
| WO | 2005025668 | A1 | 3/2005 |
| WO | 2007019115 | A1 | 2/2007 |
| WO | 2010033909 | A2 | 3/2010 |
| WO | 2011024551 | A1 | 3/2011 |
| WO | 2013055854 | A2 | 4/2013 |
| WO | 2018085598 | A1 | 5/2018 |
| WO | 2020180186 | A1 | 9/2020 |

OTHER PUBLICATIONS

Posada-Quintero, et al, "Low Impedance Carbon Adhesive Electrodes with Long Shelf Life", Annals of Biomedical Engineering, vol. 43, No. 10, Oct. 2015, (Copyright 2015), pp. 2374-2382, DOI: 10.1007/s10439-015-1282-y.

Posada-Quintero, et al., "Sensors and Actuators A: Physical", A 257 (2017), pp. 84-91, Published by Elsevier B.V., http:P/dx.doi.org/10.1016/j.sna.2017.02.023.

Syed Athar Bin Amir, et al, "Optimizing Novel ECG Electrodes", Worchester Polytechnic Institute, Apr. 25, 2013, 105 pages, Sponsored by FLEXCon.

International Search Report for PCT/EP2020/055387 mailed Apr. 9, 2020, 2 pages.

International Search Report for PCT/EP2021/072937 mailed Sep. 29, 2021, 3 pages.

Hussan et al., Development of an ionogel membrane PVA[EMIM][SCN] with enhanced thermal stability and ionic conductivity for electrochemical application, 2019, 274, pp. 402-413 (Year: 2019).

Kuhn, et al., "The Influence of Electrode Size on Selectivity and Comfort in Transcutaneous Electrical Stimulation of the Forearm," IEEE Transactions On Neural Systems and Rehabilitation Engineering, vol. 18 (3), Jun. 2010, pp. 255-262.

Keller et al., "Electrodes for transcutaneous (surface) electrical stimulation", Journal of Automatic Control, University of Belgrade, vol. 18 (2), 2008, pp. 35-45.

Isik et al., "Cholinium-based ion gels as solid electrolytes for long-term cutaneous electophysiology", Journal of Materials Chemistry C., vol. 3, received Jun. 25, 2015, Accepted Aug. 1, 2015, pp. 8942-8948.

EP Search Report for EP 19161202.7, completed Jul. 17, 2019, mailing date Jul. 19, 2025, 2 pages.

EP Search Report for EP 20194501.1, completed Nov. 6, 2020, mailing date Nov. 18, 2020, 2 pages.

\* cited by examiner

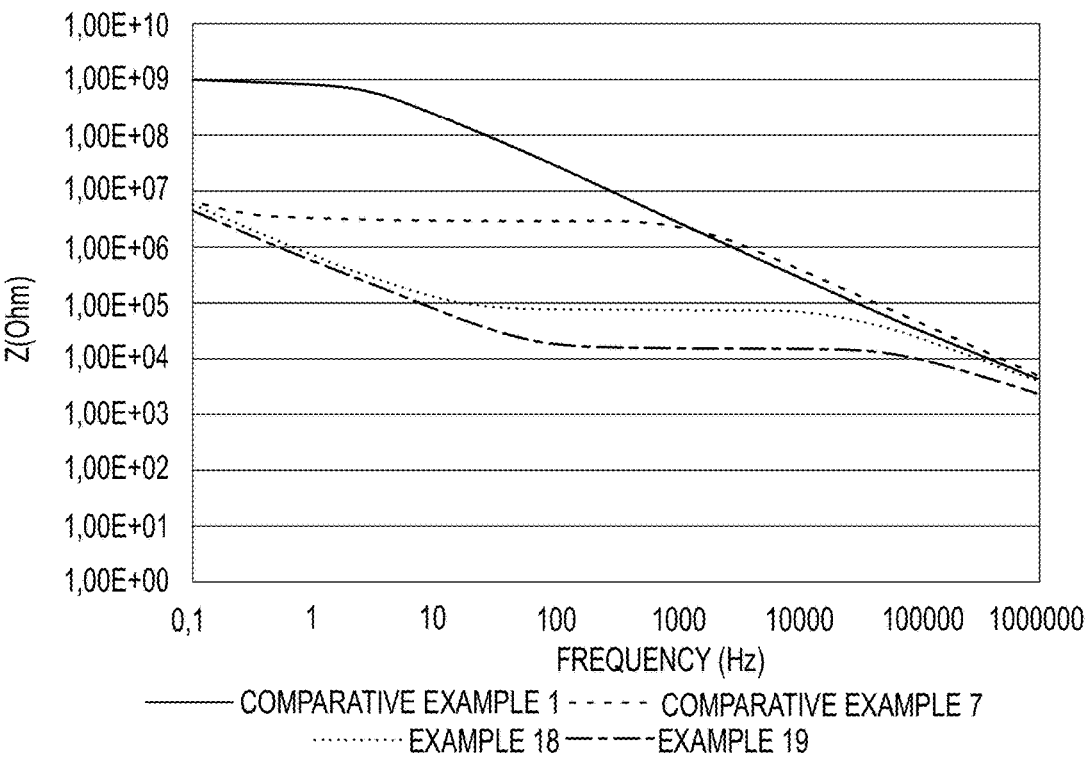
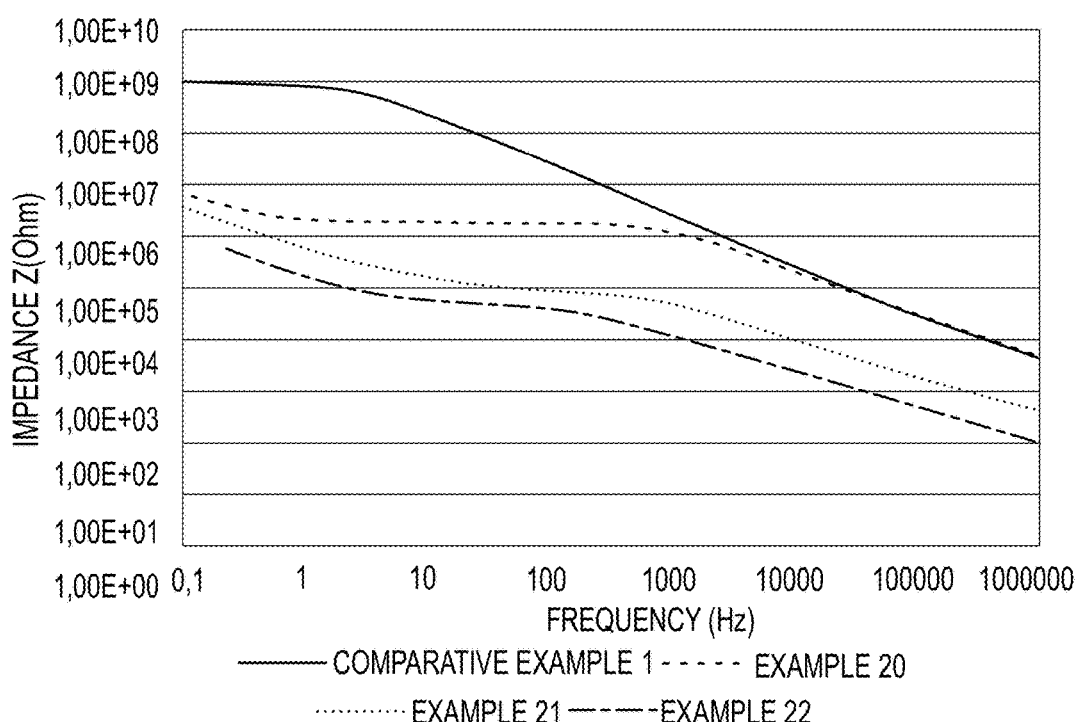
*FIG.4*
*FIG.5*

DRY ELECTRODE ADHESIVE

TECHNICAL FIELD OF THE INVENTION

The present invention relates to an electrode adhesive, which is an ionically conductive pressure sensitive adhesive allowing prolonged biosignal monitoring times without skin irritation and loss of signal quality.

BACKGROUND OF THE INVENTION

Various kinds of electrodes are used to measure biosignals such as electrocardiography (ECG), electroencephalography (EEG) and electromyography (EMG).

For example, currently used ECG electrodes are connected to the skin via gel, which acts as an electrolyte and transfers the body signal to the electrode. However, they dry out over time and cannot be used for prolonged measurements. Most of the cases, they are not recommended for use longer than 24 h. In addition, they do not have long storage times, most of the cases one month at the maximum after opening, and furthermore, they need a special packaging preventing them from drying out.

Especially currently used gel electrodes have high salt concentrations, which are needed for low impedances and good signal quality, however at the same time they cause skin irritation at many patients. Furthermore, these electrodes contain relatively high quantity of water. The high water content is one reason why these electrodes tend to dry out, and therefore, cannot be used for long-term measurements (maximum of three days), because the signal quality decreases along decreasing water content. Current gel electrodes are attached to the skin with a ring of a pressure sensitive skin adhesive surrounding the inner gel.

There are also tab electrodes currently on the market, which are attached to the skin via a gel-type adhesive. These electrodes do not need an additional skin adhesive, since the gel itself is adhering to the skin. However, these electrodes also comprise a salt and water, and can dry out over time and are therefore not suitable for prolongated measurements. The cohesion of the adhesive is often poor in these electrodes, leading to cohesive failure upon removal of the electrode.

Alternatively, a pressure sensitive adhesive comprising conductive fillers, such as carbon black can be used in the electrodes to measure biosignals. The drawback in this kind of electrodes is that a high carbon black concentration is needed, which leads to a loss in adhesion. Furthermore, the signal quality in this kind of electrodes is poor without ionically conducting adhesives.

In another electrode solution, the electrode comprises adhesives comprising the combination of carbon black and a salt. An electrophoretic alignment of conductive fillers is required in order to obtain sufficient impedances in this solution. However, this electrophoretic activation step makes the electrode production expensive and complicated.

Therefore, there is a need for electrodes to measure biosignals, which can be used for a week without loss of signal or adhesion while not drying out or sensitizing or irritating the skin.

BRIEF DESCRIPTION OF THE FIGURES

FIG. 4 is a graph illustrating impedance spectra of pressure sensitive adhesives according to the present invention containing variable amounts of PEG and 1-ethyl-3-methylimidazolium ethyl sulphate.

FIG. 5 is a graph illustrating impedance spectra of pressure sensitive adhesives according to the present invention with variation of carbon black and choline acetate.

SUMMARY OF THE INVENTION

Figure 1:
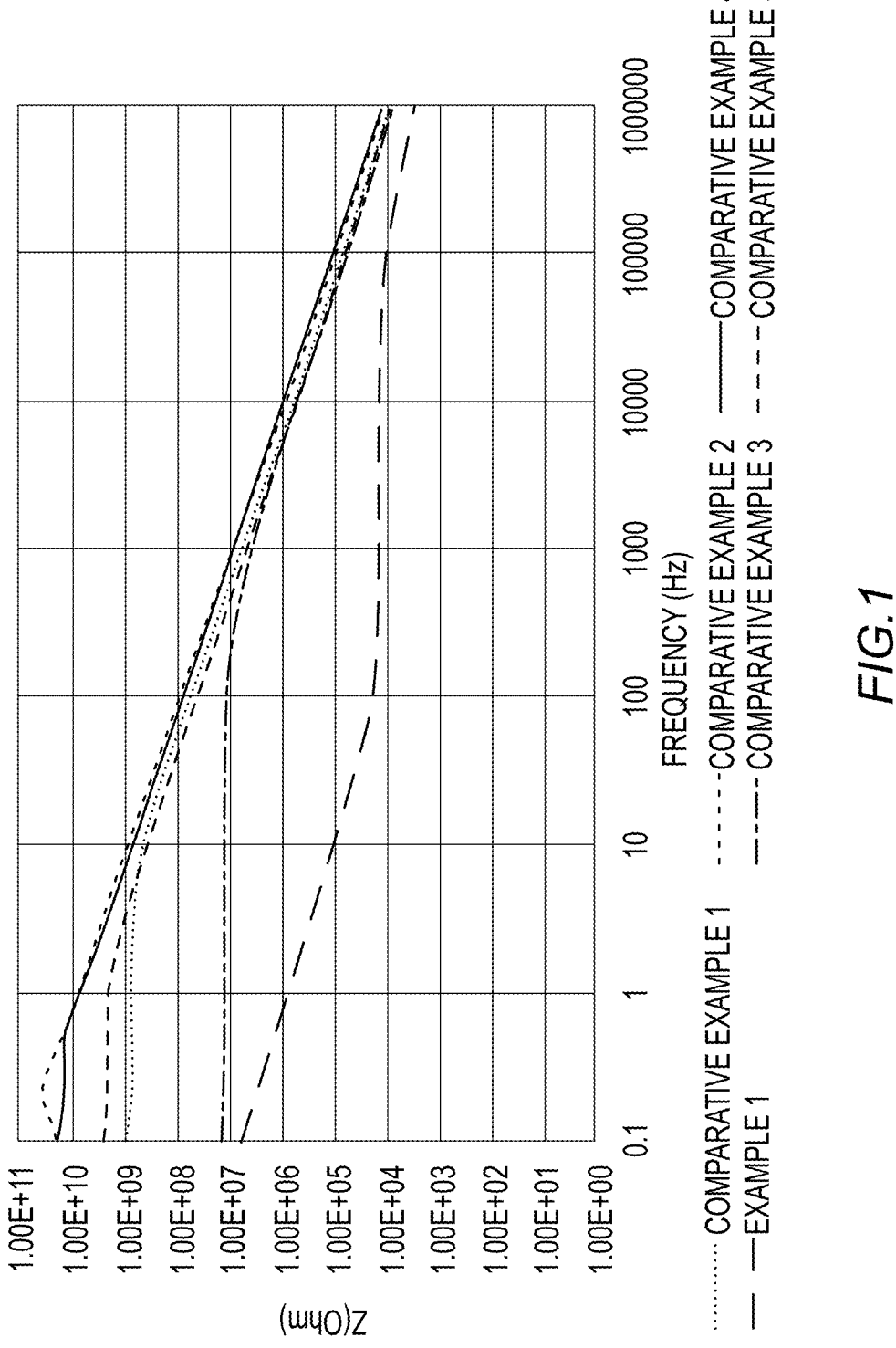
FIG. 1 is a graph illustrating impedance spectra of pressure sensitive adhesives containing different functional groups with and without 1-ethyl-3-methylimidazolium benzoate as ionic liquid.

The present invention relates to an ionically conductive pressure sensitive adhesive composition comprising a) a (meth)acrylate resin comprising at least 10% of a (meth) acrylate monomer comprising OH-group (hydroxyl group) by weight of the total weight of the (meth)acrylate resin; and b) an ionic liquid.

The present invention also relates to a dry film formed from the ionically conductive pressure sensitive adhesive composition according to the present invention.

The present invention encompasses use of an ionically conductive pressure sensitive adhesive composition or a dry film according to the present invention in skin applications as a contact medium as part of electrodes measuring biosignals from the skin.

DETAILED DESCRIPTION OF THE INVENTION

In the following passages the present invention is described in more detail. Each aspect so described may be combined with any other aspect or aspects unless clearly indicated to the contrary. In particular, any feature indicated as being preferred or advantageous may be combined with any other feature or features indicated as being preferred or advantageous.

In the context of the present invention, the terms used are to be construed in accordance with the following definitions, unless a context dictates otherwise.

As used herein, the singular forms "a", "an" and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps.

The recitation of numerical end points includes all numbers and fractions subsumed within the respective ranges, as well as the recited end points.

All percentages, parts, proportions and then like mentioned herein are based on weight unless otherwise indicated.

When an amount, a concentration or other values or parameters is/are expressed in form of a range, a preferable range, or a preferable upper limit value and a preferable lower limit value, it should be understood as that any ranges obtained by combining any upper limit or preferable value with any lower limit or preferable value are specifically disclosed, without considering whether the obtained ranges are clearly mentioned in the context.

All references cited in the present specification are hereby incorporated by reference in their entirety.

Unless otherwise defined, all terms used in disclosing the invention, including technical and scientific terms, have the meaning as commonly understood by one of the ordinary skilled in the art to which this invention belongs to. By means of further guidance, term definitions are included to better appreciate the teaching of the present invention.

The dry electrode adhesive according to the present invention is an ionically conductive pressure sensitive adhesive (PSA) with low impedance and good skin compatibility.

The ionically conductive pressure sensitive adhesive according to the present invention is based on a polar solvent-based acrylic pressure sensitive adhesive with high breathability and a non-toxic, non-irritating ionic liquid leading to ionic conductivity.

The ionically conductive pressure sensitive adhesive composition according to the present invention can be used as a dry film, which offers a solution for a long-term monitoring of biosignals by acting as a functional contact between electrode and skin. In contrast to gel-type electrodes currently in the market it cannot dry out and it does not lead to skin irritation. Furthermore, the impedance of the PSA according to the present invention is very low without any addition of water.

The present invention relates to an ionically conductive pressure sensitive adhesive composition comprising a (meth)acrylate resin comprising (meth)acrylate monomer comprising OH-group (hydroxyl group) and an ionic liquid.

An ionically conductive pressure sensitive adhesive composition according to the present invention comprises a (meth)acrylate resin comprising at least 10% of a (meth) acrylate monomer comprising OH-group by weight of the total weight of the (meth)acrylate resin.

Suitable (meth)acrylate resin for use in the present invention is preferably formed from the monomers selected from the group consisting of hydroxyethyl acrylate, hydroxypropyl acrylate, hydroxybutyl acrylate, methyl methacrylate, butyl acrylate, ethylhexylacrylate, acrylic acid, C1-C18 alkyl (meth)acrylate, (meth)acrylamide, vinyl acetate, N-vinyl caprolactam, acrylonitrile, vinyl ether, benzyl (meth) acrylate, cyclohexyl (meth)acrylate, glycidyl (meth)acrylate and mixtures thereof, preferably formed from the monomers selected from the group consisting of hydroxyethyl acrylate, methyl methacrylate, butyl acrylate, ethylhexylacrylate and mixtures thereof, and more preferably said (meth)acrylate resin is formed from hydroxyethyl acrylate, methyl (meth) acrylate, butyl acrylate and ethylhexylacrylate.

Suitable commercially available (meth)acrylate resins for use in the present invention include, but not limited to Loctite DURO-TAK 222A, Loctite DURO-TAK 87-202A; Loctite DURO-TAK 87-402A; Loctite DURO-TAK 73-626A from Henkel.

The applicant has found out that a PSA comprising a (meth)acrylate resin comprising at least 10% of a (meth) acrylate monomer comprising OH-group provides good impedance and electrodes do not dry out and they can be used for longer period measurement (the higher OH content increases the water vapor transmission rate of the polymer, which contributes to increased breathability and longer wear times).

Preferably content of said (meth)acrylate monomer comprising OH-group in said (meth)acrylate resin is at least 15% by weight of the total weight of the (meth)acrylate resin, more preferably at least 20%, more preferably at least 25%, and most preferably at least 30%, but no more than 65%, preferably no more than 60%, more preferably no more than 55%, and most preferably no more than 50%.

When the (meth)acrylate monomer comprising OH-group in said (meth)acrylate resin is more than 65% by weight of the total weight of the (meth)acrylate resin, the higher OH-group content may negatively affect the adhesion properties.

An ionically conductive pressure sensitive adhesive composition according to the present invention may comprise said (meth)acrylate resin from 5 to 80% by weight of the total weight of the composition, preferably from 15 to 75% and more preferably from 30 to 70%.

Lower (meth)acrylate resin quantity may lead to poor adhesion properties and is not beneficial to film forming properties, whereas too high quantity may lead to poor conductivity.

An ionically conductive pressure sensitive adhesive composition according to the present invention comprises an ionic liquid, preferably a non-toxic, non-irritating ionic liquid leading to ionic conductivity.

More specifically, an ionically conductive pressure sensitive adhesive composition according to the present invention comprises an ionic liquid selected from the group consisting of imidazolium acetates, imidazolium sulfonates, imidazolium chlorides, imidazolium sulphates, imidazolium phosphates, imidazolium thiocyanates, imidazolium dicyanamides, imidazolium benzoates, imidazolium triflates, choline triflates, choline saccharinate, choline sulfamates, pyridinium acetates, pyridinium sulfonates, pyridinium chlorides, pyridinium sulphates, pyridinium phosphates, pyridinium thiocyanates, pyridinium dicyanamides, pyridinium benzoates, pyridinium triflates, pyrrolidinium acetates, pyrrolidinium sulfonates, pyrrolidinium chlorides, pyrrolidinium sulphates, pyrrolidinium phosphates, pyrrolidinium thiocyanates, pyrrolidinium dicyanamides, pyrrolidinium benzoates, pyrrolidinium triflates, phosphonium acetates, phosphonium sulfonates, phosphonium chlorides, phosphonium sulphates, phosphonium phosphates, phosphonium thiocyanates, phosphonium dicyanamides, phosphonium benzoates, phosphonium triflates, sulfonium acetates, sulfonium sulfonates, sulfonium chlorides, sulfonium sulphates, sulfonium phosphates, sulfonium thiocyanates, sulfonium dicyanamides, sulfonium benzoates, sulfonium triflates, ammonium acetates, ammonium sulfonates, ammonium chlorides, ammonium sulphates, ammonium phosphates, ammonium thiocyanates, ammonium dicyanamides, ammonium benzoates, ammonium triflates and mixtures thereof.

Preferably, said ionic liquid is selected from the group consisting of 1-ethyl-3-methylimidazolium acetate, 1-ethyl-3-methylimidazolium methane sulfonate, 1-ethyl-3-methylimidazolium trifluoromethane sulfonate, 1-ethyl-3-methylimidazolium chloride, 1-ethyl-3-methylimidazolium ethyl sulphate, 1-ethyl-3-methylimidazolium diethylphosphate, 1-ethyl-3-methylimidazolium thiocyanate, 1-ethyl-3-methylimidazolium dicyanamide, 1-ethyl-3-methylimidazolium benzoate, choline trifluoromethanesulfonate, choline saccharinate, choline acesulfamate, choline N-cyclohexylsulfamate, tris(2-hydroxyethyl)methylammonium methyl sulphate, 1-ethyl-3-methylimidazolium tetrafluoroborate, 1-allyl-3-methylimidazolium bis(trifluoromethylsulfonyl) imide, choline acetate and mixtures thereof.

More preferably, the ionic liquid is selected from the group consisting of 1-ethyl-3-methylimidazolium benzoate, 1-ethyl-3-methylimidazolium tetrafluoroborate, 1-ethyl-3-methylimidazolium methane sulfonate, 1-ethyl-3-methylimidazolium chloride, 1-ethyl-3-methylimidazolium trifluoromethane sulfonate, choline trifluoromethane sulfonate, 1-ethyl-3-methylimidazolium acetate, choline acetate, 1-ethyl-3-methylimidazolium diethylphosphate, 1-allyl-3-methylimidazolium bis(trifluoromethylsulfonyl)imide, 1-ethyl-3-methylimidazolium ethyl sulphate, 1-ethyl-3-methylimidazolium thiocyanate, 1-ethyl-3-methylimidazolium dicyanamide, choline saccharinate, choline acesulfamate, and mixture thereof.

Above mentioned ionic liquids are preferred because they have good solubility to the (meth)acrylate resin according to the present invention and low toxicity.

In one embodiment two or more ionic liquids are used, in this embodiment said ionic liquids are selected from the group consisting of 1-ethyl-3-methylimidazolium acetate, 1-ethyl-3-methylimidazolium methane sulfonate, 1-ethyl-3-methylimidazolium trifluoromethane sulfonate, 1-ethyl-3-methylimidazolium chloride, 1-ethyl-3-methylimidazolium ethyl sulphate, 1-ethyl-3-methylimidazolium diethylphosphate, 1-ethyl-3-methylimidazolium thiocyanate, 1-ethyl-3-methylimidazolium dicyanamide, 1-ethyl-3-methylimidazolium benzoate, choline trifluoromethanesulfonate, choline saccharinate, choline acesulfamate, choline N-cyclohexylsulfamate, tris(2-hydroxyethyl)methylammonium methyl sulphate, 1-ethyl-3-methylimidazolium tetrafluoroborate, 1-allyl-3-methylimidazolium bis(trifluoromethylsulfonyl) imide, choline acetate;

preferably two or more ionic liquids are selected from the group consisting of 1-ethyl-3-methylimidazolium benzoate, 1-ethyl-3-methylimidazolium tetrafluoroborate, 1-ethyl-3-methylimidazolium methane sulfonate, 1-ethyl-3-methylimidazolium chloride, 1-ethyl-3-methylimidazolium trifluoromethane sulfonate, choline trifluoromethane sulfonate, 1-ethyl-3-methylimidazolium acetate, choline acetate, 1-ethyl-3-methylimidazolium diethylphosphate, 1-allyl-3-methylimidazolium bis(trifluoromethylsulfonyl)imide, 1-ethyl-3-methylimidazolium ethyl sulphate, 1-ethyl-3- methylimidazolium thiocyanate, 1-ethyl-3-methylimidazolium dicyanamide, choline saccharinate, choline acesulfamate.

Suitable commercially available ionic liquids for use in the present invention include, but are not limited to Basionics ST80, Basionics Kat1, Basionics BC01, Basionics VS11, Basionics VS03, and Efka IO 6785, all from BASF.

An ionically conductive pressure sensitive adhesive composition according to the present invention may comprise an ionic liquid from 0.1 to 35% by weight of the total weight of the composition, preferably from 0.5 to 25%, and more preferably from 1 to 15%.

If the quantity of the ionic liquid is too low, the adhesive may not show any ionic conductivity and the signal may be lost, whereas too high quantity may not provide improvement in signal quality but may increase the chances of skin irritation and decrease the adhesion properties.

An ionically conductive pressure sensitive adhesive composition according to the present invention may further comprise an ionic conductivity promoter, preferably a non-toxic, non-irritating ionic conductivity promoter leading to additional ionic conductivity.

The ionic conductivity promoter is semi-solid or solid under room temperature and can be dissolved in the ionic liquid. It has good compatibility with the (meth)acrylate resin according to the present invention.

The ionic conductivity promoter suitable for the present invention is selected from choline chloride, choline bitartrate, choline dihydrogen citrate, choline phosphate, choline gluconate, choline fumarate, choline carbonate, choline pyrophosphate, sodium chloride, lithium chloride, potassium chloride, calcium chloride, magnesium chloride, aluminum chloride, silver chloride, ammonium chlorides, alkylammonium chlorides, dialkylammonium chlorides, trialkylammonium chlorides, tetraalkylammonium chlorides and mixture thereof.

According to the present invention, the ionically conductive pressure sensitive adhesive composition according to the present invention may comprise an ionic conductivity promoter from 0.1 to 35% by weight of the total weight of the composition, preferably from 0.5 to 25%, and more preferably from 1 to 15%.

If the quantity of the ionic conductivity promoter is too low, the pressure sensitive adhesive may not show any ionic conductivity and the signal may be lost, whereas too high quantity may not provide improvement in signal quality but may increase the chances of skin irritation and decrease adhesion properties.

An ionically conductive pressure sensitive adhesive composition according to the present invention may further comprise electrically conductive particles.

Preferably electrically conductive particles are selected from the group consisting of metal particles and metal nanoparticles, metal containing particles and nanoparticles, graphite particles and nanoparticles, carbon particles and nanoparticles, carbon nanowires, conductive polymer particles and nanoparticles, and mixtures thereof, more preferably selected from the group consisting of silver containing particles, silver particles, copper particles, copper containing particles, silver nanowires, copper nanowires, graphite particles, carbon particles and mixtures thereof, and even more preferably selected from graphite particles, carbon particles and mixtures thereof.

Graphite particles and carbon particles are preferred due the fact that they do not cause skin irritation but provide adequate conductivity.

Suitable commercially available electrically conductive particles for use in the present invention include, but are not limited to Ensaco 250G, Timrex KS6 from Timcal, Printex XE2B from Necarbo, C-Nergy Super C65 from Imerys and Vulcan XC72R from Cabot.

An ionically conductive pressure sensitive adhesive composition according to the present invention may comprise said electrically conductive particles from 0.1 to 35% by weight of the total weight of the composition, preferably from 0.5 to 25%, and more preferably from 1 to 15%.

If the quantity of the electrically conductive particles is too low, it may lead to poor conductivity, whereas too high quantity may lead to loss of adhesion properties.

An ionically conductive pressure sensitive adhesive composition according to the present invention may further comprise a polyether polyol. Preferably, the polyether polyol is selected from polyethylene glycol (PEG), polypropylene glycol (PPG), polytetramethylene glycol (PTMG) and mixture thereof.

The applicant has found out that addition of polyether polyol is an exceptionally good host for ionic conductivity due to the open and flexible molecule chains, and therefore, has a positive impact on the impedance. The applicant has found out that already a small quantity of polyether polyol has a positive impact, which is beneficial regarding the skin compatibility of the composition.

Preferably, the polyether polyol may have a weight averaged molecular weight (Mw) from 300 to 1000 g/mol, preferably from 350 to 750 g/mol and more preferably from 380 to 420 g/mol, wherein the molecular weight is measured by gel permeation chromatography according to DIN 55672-1:2007-08 with THF as the eluent.

Suitable commercially available polyether polyols for use in the present invention include but are not limited to Kollisolv PEG 400 from BASF.

An ionically conductive pressure sensitive adhesive composition according to the present invention may comprise polyether polyol from 0.1 to 35% by weight of the total weight of the composition, preferably from 0.5 to 25% and more preferably from 1 to 15%.

Too high polyether polyol quantity may lead to loss of adhesion properties.

An ionically conductive pressure sensitive adhesive composition according to the present invention may further comprise a solvent.

Suitable solvent for use in the present invention may be selected from the group consisting of water, ethyl acetate, butyl acetate, butyl diglycol, 2-butoxyethanol, ethylene glycol, diethylene glycol, propylene glycol, dipropylene glycol, methanol, isopropanol, butanol, dibasic esters, hexane, heptane, 2,4-pentadione, toluene, xylene, benzene, hexane, heptane, methyl ethyl ketone, methyl isobutyl ketone, diethylether and mixtures thereof, preferably said solvent is selected from the group consisting of ethyl acetate, butyl acetate, ethylene glycol, propylene glycol and mixtures thereof.

Suitable commercially available solvents for use in the present invention include, but are not limited to ethyl acetate and ethylene glycol from Brenntag, butyl acetate from Shell Chemicals and propylene glycol from Lyondell.

An ionically conductive pressure sensitive adhesive composition according to the present invention may comprise a solvent from 10 to 90% by weight of the total weight of the composition, preferably from 20 to 80%, and more preferably from 30 to 70%.

If the quantity of the solvent is too low, this may lead to processability problems due to the fact that the viscosity is too high and (meth)acrylate resin may not be fully soluble. Whereas too high quantity may lead to loss of functionality, and the viscosity of the adhesive is too low to process.

An ionically conductive pressure sensitive adhesive composition according to the present invention has impedance value below 1,000,000 Ohm at 1000 Hz, preferably below 100,000 Ohm at 1000 Hz and more preferably below 40,000 Ohm at 1000 Hz, wherein said impedance is measured by connecting two electrodes coated each with 25 μm of an ionic conductive pressure sensitive adhesive having a contact area of 0.25 cm$^2$.

In the composition according to the present invention, the combination of the (meth)acrylate resin and the ionic liquid leads to a low impedance. The ionic liquid provides the ionic conductivity, however, if the ionic liquid is not miscible with the (meth)acrylate resin, one will not see any ionic conductivity in the pressure sensitive adhesive. In the embodiment, wherein PEG is added to the composition, the additional ether groups from the PEG make the system more polar and enhance the ionic conductivity of the ionic liquid in the (meth)acrylate resin.

An ionically conductive pressure sensitive adhesive composition according to the present invention has high breathability. Good breathability is obtained if the water can penetrate easily through the adhesive layer. To achieve this effect, a quite polar resin is required, in this occasion, the OH-functionalities support and improve the breathability.

Adhesive according to the present invention has a breathability value of about 4600 g/m$^2$ in 24 hours. As a comparison a standard acrylic PSA has a breathability value of about 2000 g/m$^2$ in 24 hours. The breathability is measured through a moisture vapor transmission rate (MVTR) measurement according to ASTM D1653.

The present invention also relates to a dry film formed from the ionically conductive pressure sensitive adhesive composition according to the present invention.

The dry film formation can be done by coating the ionically conductive pressure sensitive adhesive composition on a supporting substrate (such as a film) and drying the film in an oven at for example 120° C. for 3 minutes to remove the solvent and form a dry film of the ionically conductive pressure sensitive adhesive on the supporting substrate.

The known method used for preparing pressure-sensitive adhesive can be used. Specifically, examples include roll coating, gravure coating, reverse coating, roll brushing, spray coating, and air knife coating methods, immersing and curtain coating method, and extruding coating method with a die coater. The present invention also relates to use of an ionically conductive pressure sensitive adhesive composition according to the present invention in skin applications as a contact medium as part of electrodes measuring biosignals from the skin.

The present invention also encompasses use of a dry film according to the present invention in skin applications as a contact medium as part of electrodes measuring biosignals from the skin.

Impedance is the key parameter for the functionality of electrodes. The requirements and measurement procedures for disposable ECG electrodes are defined by ANSI/AAMI EC12:2000/(R)2015. The impedance of the electrodes at 10 Hz is required to be below 2000 Ohm on average for two electrodes attached to each other with their adhesive sides.

Electrodes comprising ionically conductive pressure sensitive adhesive according to the present invention have impedance value below 100,000 Ohm at 10 Hz, preferably below 10,000 Ohm at 10 Hz and more preferably below 2,000 Ohm at 10 Hz, wherein said impedance is measured by attaching two electrodes to each other with their adhesive sides.

Another important test for ECG electrode is the Defibrillation Overload Recovery (DOR) (measured according to ANSI/AAMI EC12:2000/(R)2015). In this context, defibrillation overload recovery refers to the voltage decrease across the electrodes while a 10 μF capacitor (charged to 200V) is discharged via the sample (which consists of two electrodes attached to each other via their adhesive sides; electrode corresponds here to an adhesive on an Ag/AgCl conductive layer on a non-conductive substrate). For a successful test this has to be fulfilled 3 times in a row. The allowed voltage ranges are shown in the Table 1 below, values are either maximum allowed voltages at a time or maximum allowed voltage differences within a time interval:

TABLE 1

| Time | Need (mV) | |
|---|---|---|
| 2 s | < | 2000 |
| 7 s | < | 100 |
| 7-17 s | <Δ | 11 |
| 17-27 s | <Δ | 11 |

The defibrillation overload recovery may be influenced by the selection of the ionic liquid/salt, especially the anion of the ionic liquid/salt. Chloride provides fast defibrillation overload recovery times on Ag/AgCl electrodes. In principle, every chloride may be used, however, chlorides of ionic liquids (e.g. EMIM chloride or choline chloride) are preferred due to their good compatibility with the adhesive material. However, EMIM chloride in the adhesive composition may not lead to sufficient bulk conductivity to pass the impedance requirements. Surprisingly, ionic liquids with anions providing good bulk conductivity (e.g. EMIM dicyanamide) do not show a fast defibrillation overload recovery. Therefore, there is a need to find a good balance between good bulk conductivity and fast discharge properties for the ideal electrode behaviour. A combination of two or more different ionic liquids or salts in an ionically conductive PSA according to the present invention may be a solution to meet all performance requirements of electrodes.

It has been found that chloride salts provide fast discharge properties already in lower quantities (<2 wt % of the dry adhesive film according to the present invention) because electrodes with adhesives comprising chlorides have a DC resistance in the kOhm range, whereas electrodes with adhesives without chlorides have a DC resistance about 10 MOhm. Only a low DC resistivity allows the sample to discharge in a short time, and therefore, the defibrillation overload recovery requirement can be met.

In the composition according to the present invention, the combination of the (meth)acrylate resin and the ionic liquid (s) leads to a fast discharge of electrode samples and the defibrillation overload requirements are met for electrodes with matched interface between adhesive and conductive layer.

EXAMPLES

Materials:
1) LOCTITE DURO-TAK 222A, LOCTITE DURO-TAK 1053 and LOCTITE DURO-TAK 387-2518 from Henkel AG & Co. KGaA
2) LOCTITE EDAG 6038E SS from Henkel AG & Co. KGaA

10

3) 1-ethyl-3-methylimidazolium benzoate from BASF
4) 1-ethyl-3-methylimidazolium trifluoromethanesulfonate from Proionic
5) 1-ethyl-3-methylimidazolium dicyanamide from BASF
6) 1-ethyl-3-methylimidazolium chloride from BASF
7) 1-ethyl-3-methylimidazolium tetrafluoroborate from Sigma-Aldrich
8) 1-ethyl-3-methylimidazolium methanesulfonate from Proionic
9) 1-ethyl-3-methylimidazolium diethylphosphate from IoLiTec
10) AMIM bis(trifluoromethylsulfonyl)imide from Sigma-Aldrich
11) 1-ethyl-3-methylimidazolium ethyl sulphate from BASF
12) 1-ethyl-3-methylimidazolium thiocyanate from BASF
13) PEG400 from Fluka
14) Choline chloride from Sigma-Aldrich
15) Choline hydroxide solution from Sigma-Aldrich
16) Saccharine Sodium Hydrate from Sigma-Aldrich
17) Triflic Acid Sigma-Aldrich
18) Acesulfam K from Sigma-Aldrich
19) C-Nergy Super C65 from Imerys
20) Hydrogenated tallow alkyl(2-ethylhexyl)dimethyl ammonium methylsulfate from Akzo Nobel (Arquad HTL8-MS)
21) Choline triflate was prepared according to *Chem. Commun.*, 2011, 47, 6401-6403.
22) Choline saccharinate and choline acesulfamate were prepared according to *J. Phys. Chem. B* 2007, 111, 19, 5254-5263.

Example 1 and Comparative Examples 1-5

Impedance of an Ionic Liquid in Pressure Sensitive Adhesives with Different Functionality Example 1

2 g Loctite DURO-TAK 222A (solid content: 41%) and 0.091 g of 1-ethyl-3-methylimidazolium benzoate were mixed in a conditioning mixer for 3 minutes at 2000 rpm.

Comparative Example 3

2 g Loctite DURO-TAK 1053 (solid content: 48%) and 0.108 g of 1-ethyl-3-methylimidazolium benzoate were mixed in a conditioning mixer for 3 minutes at 2000 rpm.

Comparative Example 5

2 g Loctite DURO-TAK 387-2516 (solid content: 42%) and 0.094 g of 1-ethyl-3-methylimidazolium benzoate were mixed in a conditioning mixer for 3 minutes at 2000 rpm.

Comp. Ex. 1, 2 and 4 contained no ionic liquid. The mixtures were coated onto a release liner and dried at room temperature for 30 min yielding PSA films with a thickness of 20 μm. Subsequently the drawdown was cured at 120° C. for 3 min and covered with another release liner. Table 2 lists the (meth)acrylate resin and ionic liquid used in the mixtures, OH-functionality of the (meth)acrylate resin (the amount of OH-functional (meth)acrylate monomers by weight of the total weight of the (meth)acrylate resin), and the amount of ionic liquid (% by weight of the dry PSA film).

TABLE 2

1-ethyl-3-methylimidazolium benzoate (EMIM benzoate) PSA samples

| | (Meth)acrylate resin | OH-Functionality (wt. %) | Ionic liquid | Ionic liquid amount (wt. %) |
|---|---|---|---|---|
| Comparative Example 1 | DURO-TAK 222A | >20 | — | — |
| Example 1 | | | EMIM benzoate | 10 |
| Comparative Example 2 | DURO-TAK 1053 | <10 | — | — |
| Comparative Example 3 | | | EMIM benzoate | 10 |
| Comparative Example 4 | DURO-TAK 387-2516 | <10 | — | — |
| Comparative Example 5 | | | EMIM benzoate | 10 |

For impedance measurements (FIG. 1) the dried PSA films were transferred onto an Aluminium (Al) foil. Two pieces of the PSA-Al film were cut and stuck together to form an Al-PSA-Al capacitor with an area of 0.25 cm$^2$ and 40 µm PSA thickness. The impedance was measured with a potentiostat from Metrohm Autolab at a frequency range from $9\times10^5$ to 0.1 Hz. FIG. 1 shows that a high degree of OH functionalization leads to a lower impedance especially in combination with ionic liquids.

Examples 2-15 and Comparative Example 6

Comparison of Ionic Liquids in Pressure Sensitive Adhesive with High OH Functionality 5 g Loctite DURO-TAK 222A (solid content: 41%) and 0.228 g of various ionic liquids, according to Table 3, were mixed in a conditioning mixer for 3 minutes at 2000 rpm.

The mixtures (Table 3) were coated onto a release liner and dried at room temperature for 30 min yielding PSA films with a thickness of 20-30 µm. Subsequently the drawdown was cured at 120° C. for 3 min and covered with another release liner.

Impedance Measurement:

For impedance measurements (FIG. 2) the dried PSA films were transferred onto an Al foil. Two pieces of the PSA-Al film were cut and stuck together to form an Al-PSA-Al capacitor with an area of 0.25 cm$^2$ and 40-60 µm PSA thickness. The impedance was measured with a potentiostat from Metrohm Autolab at a frequency range from $9\times10^5$ to 0.1 Hz.

Figure 2:
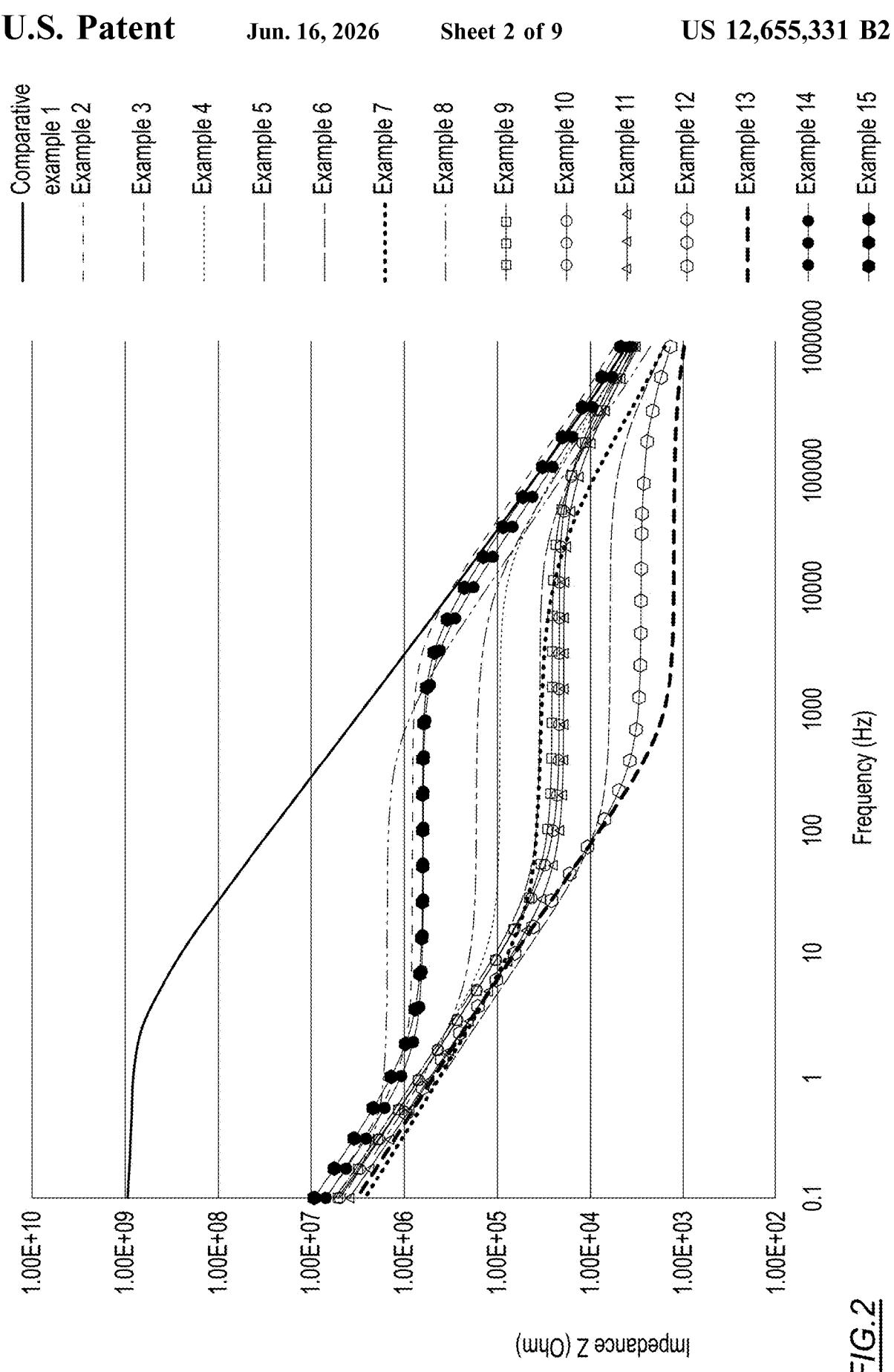
FIG. 2 is a graph illustrating impedance spectra of pressure sensitive adhesives containing various ionic liquids according to the present invention.

FIG. 2 illustrates that the addition of ionic liquids to an OH functionalized pressure sensitive adhesive reduces the impedance significantly. The plateau which can be seen in the curves corresponds to the bulk resistance of the adhesive and is shifted to lower values by the ionic liquids. Ionic liquids with biggest impact on the impedance reduction are EMIM dicyanamide, EMIM thiocyanate and EMIM triflate.

Skin Compatibility Study:

The skin compatibility of the pressure sensitive adhesive composition was measured in an in-vitro skin irritation test using an OS-REp model (Open Source Reconstructed Epidermis). 25 µL of the active pressure sensitive adhesive composition was applied to the epidermis model. After 42 h

TABLE 3

DURO-TAK 222A with various ionic liquids

| | (Meth)acrylate resin | Ionic liquid | Ionic liquid amount (wt. %) |
|---|---|---|---|
| Comparative Example 1 | DURO-TAK 222A | — | — |
| Example 2 | DURO-TAK 222A | EMIM tetrafluoroborate | 10 |
| Example 3 | DURO-TAK 222A | EMIM methanesulfonate | 10 |
| Example 4 | DURO-TAK 222A | EMIM chloride | 10 |
| Example 5 | DURO-TAK 222A | EMIM trifluoromethanesulfonate | 10 |
| Example 6 | DURO-TAK 222A | Choline trifluoromethanesulfonate | 10 |
| Example 7 | DURO-TAK 222A | EMIM acetate | 10 |
| Example 8 | DURO-TAK 222A | Choline acetate | 10 |
| Example 9 | DURO-TAK 222A | EMIM diethylphosphate | 10 |
| Example 10 | DURO-TAK 222A | AMIM bis(trifluoromethylsulfonyl)imide | 10 |
| Example 11 | DURO-TAK 222A | EMIM ethyl sulphate | 10 |
| Example 12 | DURO-TAK 222A | EMIM thiocyanate | 10 |
| Example 13 | DURO-TAK 222A | EMIM dicyanamide | 10 |
| Example 14 | DURO-TAK 222A | Choline saccharinate | 10 |
| Example 15 | DURO-TAK 222A | Choline acesulfamate | 10 |
| Comparative Example 6 | DURO-TAK 222A | Hydrogenated tallow alkyl(2-ethylhexyl)dimethyl ammonium methylsulfate | 10 | incubation and 3 h incubation with MTT (200 µl, 1 mg/ml MTT (3-(4,5-Dimethylthiazol-2-yl)-2,5-diphenyltetrazolium bromide)), a formazan extraction was performed and the optical density at 570-590 nm was measured. The relative vitality of the cells was calculated by the optical density.

The skin irritation test is a modified version of an OS-REp test according to OECD TG 439 which is a protocol for the identification of irritant neat substances and salts.

The usual contact time of the potential irritant with the skin model is 35 min. Subsequently the substance to be tested will be washed off and an incubation time of 42 h seconds and can be viewed by a software Heartscan 2.0 provided by MedX5.

Figure 3A:
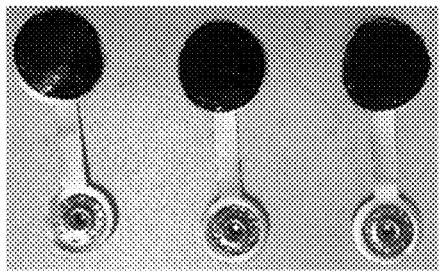
FIG. 3a is a photograph of silver electrodes coated with ionically conductive pressure sensitive adhesives according to the present invention containing additional carbon black conductive particles.

For preparation of the dry electrodes silver electrodes were printed using a commercial Henkel silver ink Loctite ECI 1010 E&C and laminated with an ionically conductive PSA according to the present invention. FIG. 3a illustrates an electrode set used for an ECG measurement. The electrodes were laminated with a PSA filled with an ionic liquid (adhesive according to the present invention) and carbon black for better visibility. ECG spectra of PSAs filled with different concentrations of EMIM acetate (Table 5) were recorded.

TABLE 5

| | | | Ionic liquid amount (wt. %) | Electrode setup (material; surface area) |
|---|---|---|---|---|
| | (Meth)acrylate resin | Ionic liquid | | |
| Example 16 | DURO-TAK 222A | EMIM acetate | 5 | Ag; 2.84 cm$^2$ |
| Example 7 | | | 10 | |
| Example 17 | | | 15 | |

*Samples for ECG signal monitoring* starts. For a relative vitality of the cells >50% the substance can be considered being non-irritant.

Due the fact that pressure-sensitive adhesives were tested, which cannot be washed off, the contact time was significantly longer—42 h instead to 35 min—indicating that the present test conditions were harsher. Table 4 illustrates the results, which show that the conductive PSAs have a very good skin compatibility. In contrast to the adhesives according to the present invention, comparative example 6 containing a quaternary ammonium salt instead of an ionic liquid shows an increased irritation potential.

TABLE 4

Overview of In-Vitro skin irritation results

| | Vitality (%, according to epidermis test) |
|---|---|
| Comparative Example 1 | 86 ± 4 |
| Example 1 | 78 ± 4 |
| Example 8 | 84 ± 8 |
| Example 11 | 63 ± 8 |
| Example 12 | 95 ± 18 |
| Example 13 | 80 ± 10 |
| Comparative Example 6 | 20 ± 8 |

Examples 7, 16 and 17

ECG Signal Monitoring

ECG measurements were performed on a portable MedX5 ECG device, which can be used with all kinds of standard electrodes. ECG spectra were recorded over a period of 30

Figure 3B:
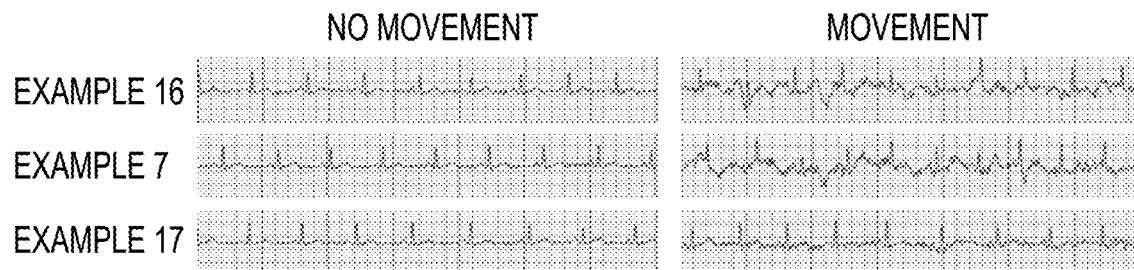
FIG. 3b illustrates ECG spectra recorded with silver electrodes connected to the skin via ionically conductive pressure sensitive adhesives containing 1-ethyl-3-methylimidazolium acetate.

FIG. 3b illustrates the recorded ECG spectra. ECG signals were recorded using three electrodes (working-, counter- and reference electrode) placed at the inner side of the human forearms (two on the left arm, one on the right arm) and the derivation was measured between left and right arm. The monitoring took place while resting the arms (no movement) and moving the arms continuously up and down (movement). In all cases good ECG signals were obtained especially for the higher ionic liquid concentrations.

Examples 18-19 and Comparative Example 7

Enhancement of Ionic Conductivity in PSA: PEG400 Blends

Comparative Example 7

4.15 g Loctite DURO-TAK 222A (solid content: 41%), 0.3 g PEG400 (Sigma Aldrich) and 0.29 g ethyl acetate were mixed in a conditioning mixer for 3 minutes at 2000 rpm.

Example 18

4.88 g Loctite DURO-TAK 222A (solid content: 41%) and 0.1 g 1-ethyl-3-methylimidazolium ethyl sulphate were mixed in a conditioning mixer for 3 minutes at 2000 rpm.

Example 19

4.15 g Loctite DURO-TAK 222A (solid content: 41%), 0.3 g PEG400, 0.1 g 1-ethyl-3-methylimidazolium ethyl sulphate and 0.43 g ethyl acetate were mixed in a conditioning mixer for 3 minutes at 2000 rpm.

The mixtures (Table 6) were coated onto a release liner and dried at room temperature for 30 min yielding PSA films with a thickness of 20 µm. Subsequently the drawdown was cured at 120° C. for 3 min and covered with another release liner.

TABLE 6

| | (Meth)acrylate resin | PEG400 (wt. % of dry PSA film) | Ionic liquid | Ionic liquid amount (wt. %) |
|---|---|---|---|---|
| DURO-TAK 222A PEG400 blends with and without EMIM ethyl sulphate | | | | |
| Comparative Example 1 | DURO-TAK 222A | — | — | — |
| Comparative Example 7 | DURO-TAK 222A | 15 | — | — |
| Example 18 | DURO-TAK 222A | | EMIM ethyl sulphate | 5 |
| Example 19 | DURO-TAK 222A | 15 | EMIM ethyl sulphate | 5 |

For impedance measurements (FIG. 4) the dried PSA films were transferred onto an Al foil. Two pieces of the PSA-Al film were cut and stuck together to form an Al-PSA-Al capacitor with an area of 0.25 cm$^2$ and 40 μm PSA thickness. The impedance was measured with a potentiostat from Metrohm Autolab at a frequency range from $9 \times 10^5$ to 0.1 Hz.

Examples 20-22

Addition of Carbon Black to an Ionic Conductive Pressure Sensitive Adhesive

Example 20

9.79 g Loctite DURO-TAK 222A (solid content: 41%) and 0.22 g of choline acetate were mixed in a conditioning mixer for 3 minutes at 2000 rpm.

Example 21

0.45 g carbon black (C-Nergy Super C65) and 1.36 g butyl acetate were mixed in the speedmixer using glass beads (3 min, 3500 rpm) to prepare a paste. 9.32 g Loctite DURO-TAK 222A was added in steps of 0.5 g per addition. After each PSA addition step the composition was mixed in the speedmixer for 1 min at 3500 rpm. Afterwards, 0.23 g of choline acetate was added and mixed in a conditioning mixer for 3 minutes at 2000 rpm.

Example 22

0.70 g carbon black (C-Nergy Super C65) and 2.5 g butyl acetate were mixed in the speedmixer using glass beads (3 min, 3500 rpm) to prepare a paste. 9.07 g Loctite DURO-TAK 222A was added in steps of 0.5 g per addition. After each PSA addition step the composition was mixed in the speedmixer for 1 min at 3500 rpm. Afterwards, 0.23 g of choline acetate was added and mixed in a conditioning mixer for 3 minutes at 2000 rpm.

The mixtures (Table 7) were coated onto a release liner and dried at room temperature for 30 min yielding PSA films with a thickness of 20 μm. Subsequently the drawdown was cured at 120° C. for 3 min and covered with another release liner.

TABLE 7

| | (Meth)acrylate resin | Ionic liquid | Ionic liquid amount (wt. %) | Carbon black amount (wt. % of dry PSA film) |
|---|---|---|---|---|
| DURO-TAK 222A containing choline acetate and different amounts of carbon black | | | | |
| Comparative Example 1 | DURO-TAK 222A | — | — | — |
| Example 20 | DURO-TAK 222A | Choline acetate | 5 | — |
| Example 21 | DURO-TAK 222A | Choline acetate | 5 | 10 |
| Example 22 | DURO-TAK 222A | Choline acetate | 5 | 15 |

For impedance measurements (FIG. 5) the dried PSA films were transferred onto an Al foil. Two pieces of the PSA-Al film were cut and stuck together to form an Al-PSA-Al capacitor with an area of 0.25 cm² and 40 μm PSA thickness. The impedance was measured with a potentiostat from Metrohm Autolab at a frequency range from 9×10⁵ to 0.1 Hz.

Example 23

Impedance of Paired Electrodes with Dry Electrode Adhesives Having Combinations of Ionic Liquids 5 g LOCTITE DURO-TAK 222A (solid content: 41%) and 0.171 g of 1-ethyl-3-methylimidazolium trifluoromethanesulfonate and 0.057 g of 1-ethyl-3-methylimidazolium chloride were mixed in a conditioning mixer for 3 minutes at 2000 rpm. The mixture was coated onto a release liner and dried at room temperature for 30 min yielding PSA films with a thickness of 20 μm. Subsequently the drawdown was cured at 120° C. for 3 min and covered with another release liner.

For impedance measurements electrodes were prepared by transferring the dried PSA films to TPU substrates coated with Ag/AgCl layer (Loctite EDAG 6038E SS from Henkel). Electrodes with an area of 3.1 cm² were cut and attached to each other to form an Ag/AgCl-PSA-Ag/AgCl capacitor with an area of 3.1 cm² and 40 μm PSA thickness. The electrode pair was connected with alligator clips and the impedance of the capacitor was measured with a potentiostat from Metrohm Autolab at a frequency range from 9×10⁵ to 0.01 Hz.

Figure 6:
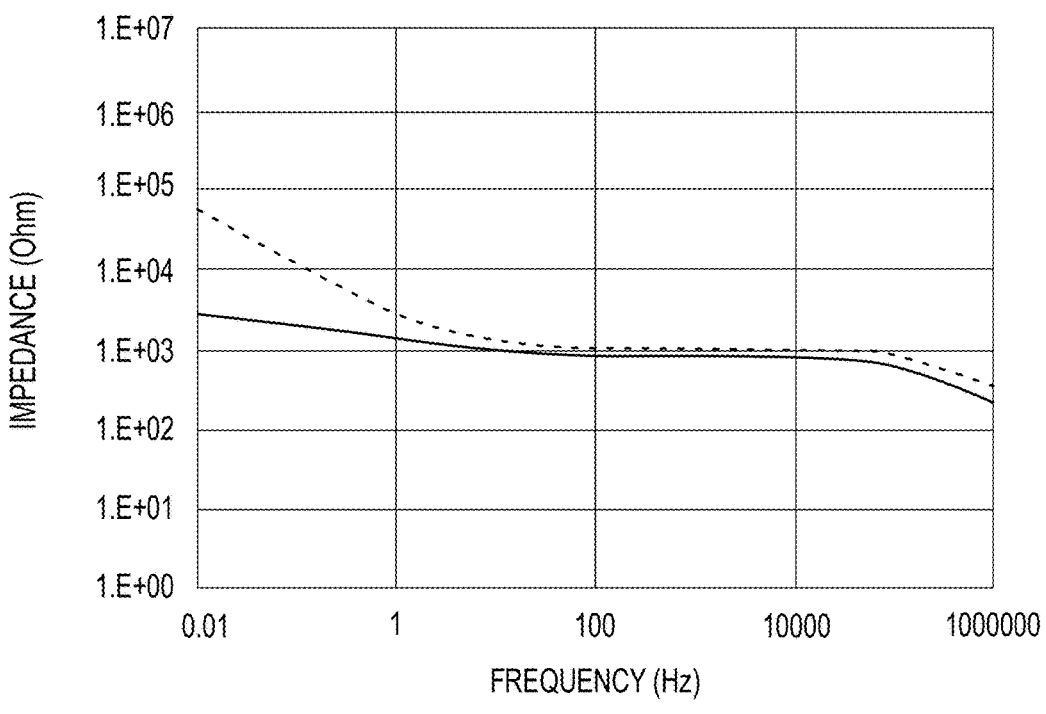
FIG. 6 is a graph illustrating impedance spectra of compositions according to Example 23 (solid line) and 5 (dotted line) on Ag/AgCl electrodes.

FIG. 6 illustrates impedance spectra of electrodes with dry adhesive compositions according to Example 23 (solid line) and example 5 (dotted line). Impedance spectra of electrodes with Ag/AgCl conductive layer without chloride in the adhesive show a strong capacitive increase at low frequencies corresponding to the existence of a blocking electrode and therefore a high DC resistance since (almost) no charge transfer across the electrode/adhesive interface occurs. In contrast to that, electrodes with adhesives comprising chloride allow reactions between the Ag/AgCl conductive layer and the electrode adhesive leading to charge transfer (at suitable low voltages) and therefore low DC resistance which enables a fast discharge during DOR (defibrillation overload recovery) experiments.

Figure 7:
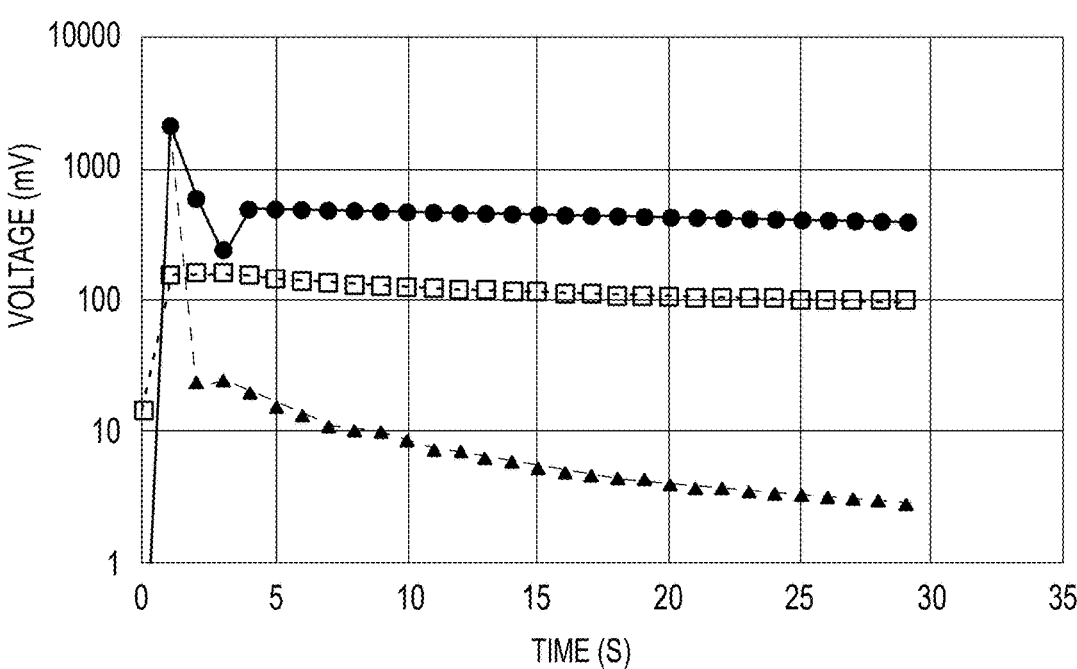
FIG. 7 is a graph illustrating defibrillation overload recovery test curves of Examples 4, 5, 13.

Defibrillation overload recovery was tested for Examples 4, 5, and 13. In this test voltage over time during discharge for different electrode adhesive compositions (Example 5 (circles), Example 13 (squares), Example 4 (triangles)) was measured. FIG. 7 shows the voltage across the electrodes during discharge. For Examples 5 and 13 the voltage is constantly above 100 mV indicating that no sufficient discharge takes place (condition 2 of table 7 is missed <100 mV after 7 s) whereas sample 4 easily passes the test requirements.

Figure 8:
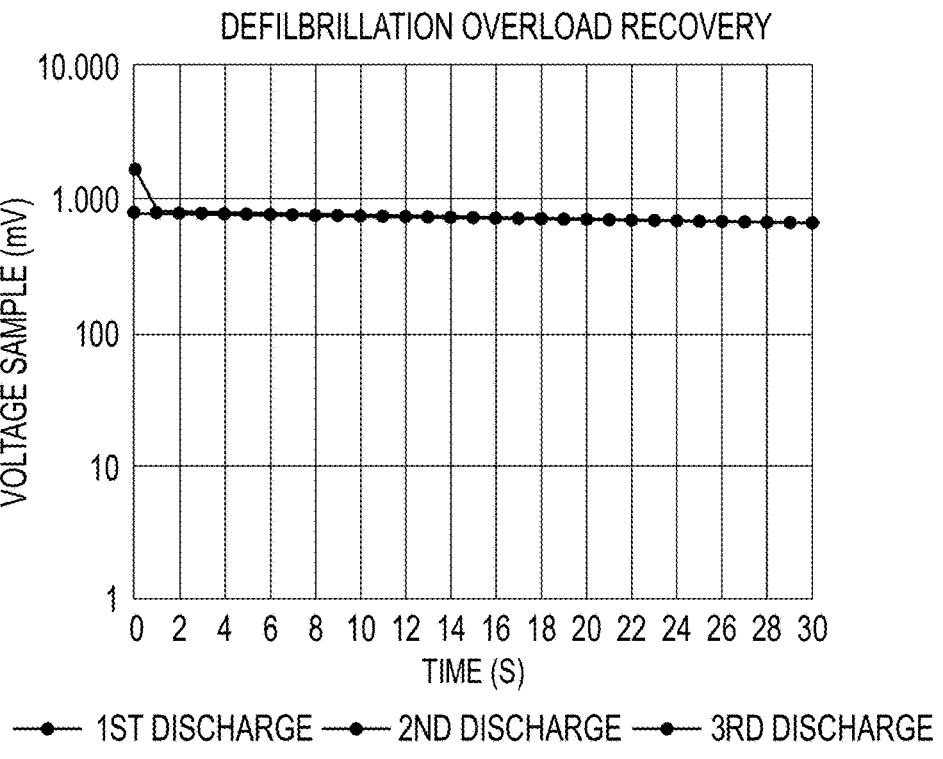
FIG. 8 is a graph illustrating defibrillation overload recovery discharge curves according to ANSI/AAMI EC12:2000/(R)2015 for an electrode pair with electrode adhesive according to Example 5.

FIG. 8 illustrates three consecutive defibrillation overload recovery discharge curves according to ANSI/AAMI EC12: 2000/(R)2015 for an electrode pair with electrode adhesive according to the Example 5. An overview of test conditions for an electrode pair with electrode adhesive according to the Example 5 is illustrated in table 8 below. Three out of four requirements are not met showing the need for an adhesive that allows a faster discharge.

TABLE 8

| | | Example 2 | | |
| | | 1st discharge | 2nd discharge | 3rd discharge |
| Time | Need (mV) | | | |
| --- | --- | --- | --- | --- |
| 2 s | < 2000 | 759 | 765 | 5 |
| 7 s | < 100 | 718 | 730 | 734 |
| 7-17 s | <Δ 11 | 39 | 29 | 25 |
| 17-27 s | <Δ 11 | 25 | 21 | 16 |

Figure 9:
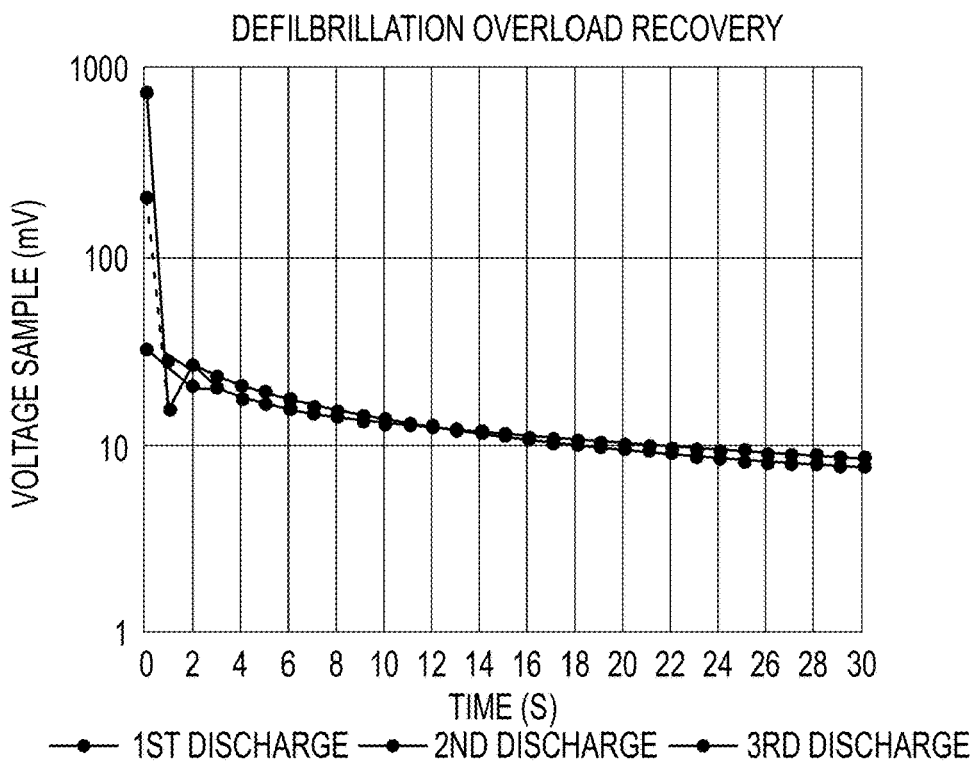
FIG. 9 is a graph illustrating defibrillation overload recovery discharge curves according to ANSI/AAMI EC12:2000/(R)2015 for an electrode pair with electrode adhesive according to Example 23.

FIG. 9 illustrates three consecutive defibrillation overload recovery discharge curves according to ANSI/AAMI EC12: 2000/(R)2015 for an electrode pair with electrode adhesive according to the Example 23. An overview of test conditions for an electrode pair with electrode adhesive according to the Example 23 is illustrated in table 9 below.

TABLE 9

| | | Example 2 | | |
| | | 1st discharge | 2nd discharge | 3rd discharge |
| Time | Need (mV) | | | |
| --- | --- | --- | --- | --- |
| 2 s | < 2000 | 26.9 | 25.9 | 20.2 |
| 7 s | < 100 | 15.8 | 15.4 | 14.6 |
| 7-17 s | <Δ 11 | 5.7 | 4.6 | 4 |
| 17-27 s | <Δ 11 | 2.3 | 2.1 | 1.7 |

Here all requirements were met showing the benefit of adding a DC conductivity enabling ionic liquid having a chloride as an anion.

ANSI/AAMI EC12:2000/(R)2015 describes that the use time of an electrode is limited to the time a sample (two electrodes attached to each other via their adhesive sides) can be biased with 200 nA current at a resulting voltage <100 mV. A DC offset >100 mV should not be measured. This value correlates to the starting points of the current bias curves.

Figure 10:
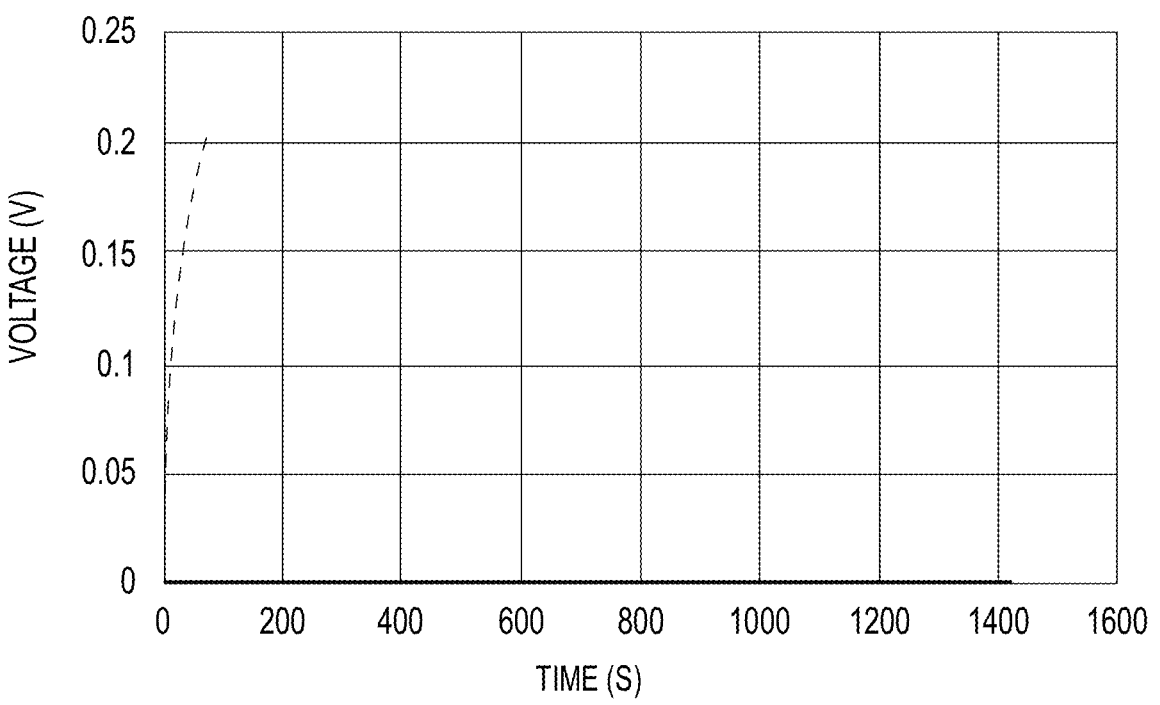
FIG. 10 is a graph illustrating a voltage increase during current bias for electrode samples with different adhesive compositions (Examples 5 and 23).

FIG. 10 illustrates a voltage increase during current bias for electrode samples with different adhesive compositions according to the present invention: Example 23—solid line and Example 5—dotted line.

Example 23 corresponds to a sample with DC conductivity. The voltage is defined by Ohm's law. This voltage can be maintained for a long time. Since DC conductivity corresponds to a reversible electrochemical reaction at the interface, the voltage will stay relatively constant as long as reactants are available at the interface. Example 5 does not provide significant DC conductivity across the interface. Therefore, the voltage corresponds to a charging of the interface capacitance and is therefore significantly increasing with time.

Electrodes that provide a DC conductivity also show longer current bias tolerance and lower DC offset values. Preferably, electrode adhesives show both DC conductivity and low impedance.

Figure 11:
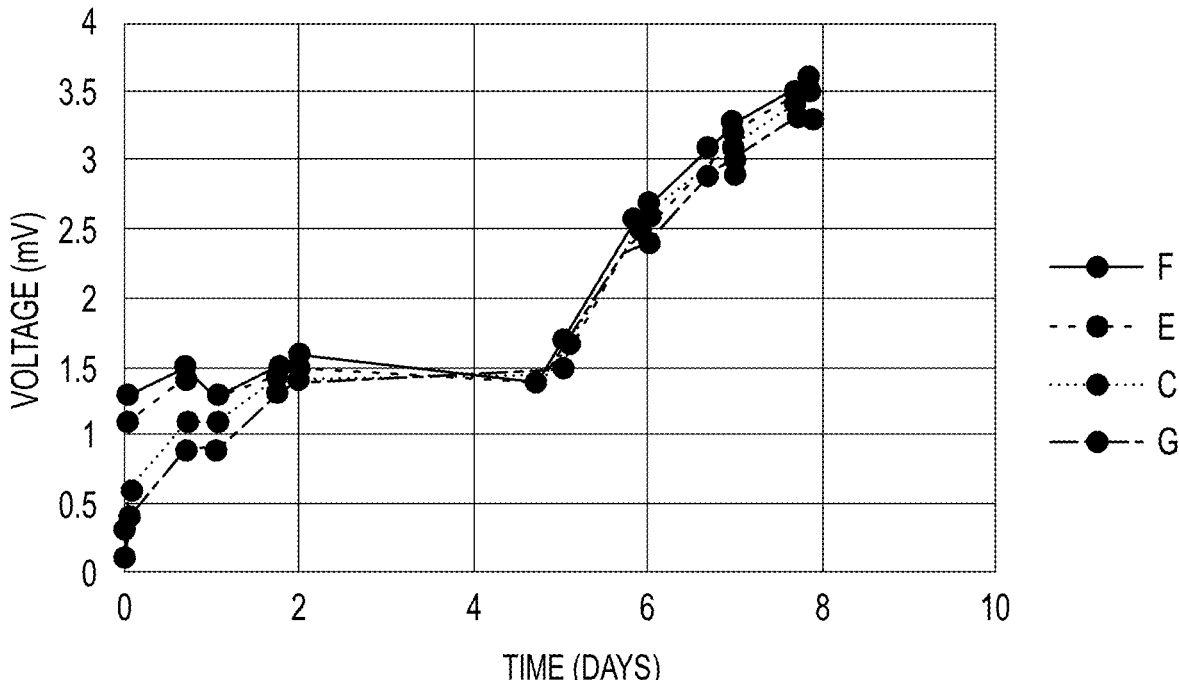
FIG. 11 is a graph illustrating a voltage increase during long time current bias (200 nA) for electrode samples having an electrode adhesive (Example 23).

FIG. 11 illustrates a voltage increase during long time current bias (200 nA) for electrode samples having an electrode adhesive according to the present invention (Example 23).

Due to the long measurement time the voltage here was not continuously logged but measured only a few times a day (with breaks for weekend). The samples F, E, C, G correspond to nominally identical samples which have been current biased while being series connected. Therefore, the results are very similar as expected. An initial variation (DC offset) vanishes after two days leading to stable plateau.

After about 5 days the voltage starts to increase. However, the voltage is still well below the required limit of 100 mV. Therefore, this test was clearly passed for the 8 days measurement (and would be most likely also passed for longer times).

Figure 12:
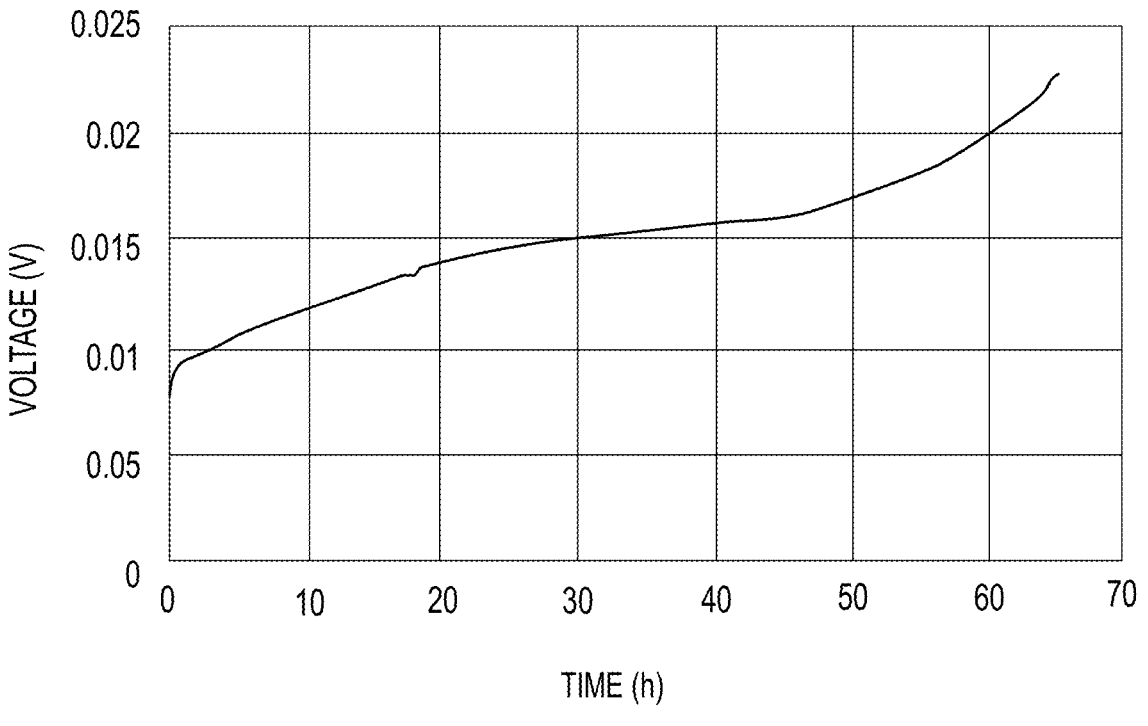
FIG. 12 is a graph illustrating a voltage increase during long time current bias (2 μA) for an electrode sample having an electrode adhesive (Example 23).

FIG. 12 illustrates a voltage increase during long time current bias (2 μA) for an electrode sample having an electrode adhesive (Example 23).

2 μA corresponds to ten times the current required by the norm. This test aims at qualifying an accelerated test. The results are roughly corresponding with an increase occurring from 40-45 h. With factoring in the higher current (and figuring that the relevant value is the flown charge) that would correspond to 6 days in the normal test (where 5 days were seen). The voltages here were higher due to Ohm's law (and therefore the beginning of the increase might be hidden).

ANSI/AAMI EC12:2000/(R)2015 requires a peak-to-peak voltage of less than 150 μV (after 1 min stabilization) to guarantee a low noise ECG signal. The AC signal of an electrode sample with electrode adhesive recorded via an ECG system usually has a peak-to-peak voltage below 10 μV.

Figure 13:
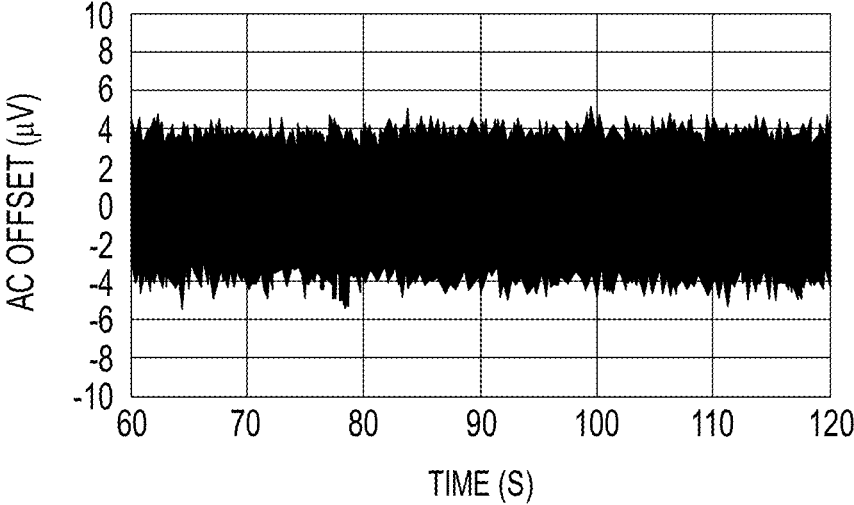
FIG. 13 illustrates an offset instability and internal noise measurement for an electrode sample having an electrode adhesive according to the present invention (Example 23).

FIG. 13 illustrates an offset instability and internal noise measurement for an electrode sample having an electrode adhesive according to the present invention (Example 23).

The measurement corresponds to an ECG measurement with interconnected electrodes instead of a human body. The total bandwidth was about 8 μV and therefore much lower than required in the norm (150 μV).

Example 24

Impedance of Paired Electrodes with Dry Electrode Adhesives Having Different Degrees of OH Functionality Impedance of paired electrodes with dry electrode adhesives according to the present invention comprising 10 wt. % EMIM-salt and a (meth)acrylate resin comprising different quantities of a (meth)acrylate monomer comprising OH-group; the following quantities according to the present invention were tested: 15.0 wt. %, 18.8 wt. %, 22.5 wt. %, 30.0 wt. % and 50.0 wt. % and were compared to quantities 0 wt. % and 7.5 wt. %. The impedance values were normalised to a film thickness of 30 μm and an area of 4 cm². The test results are illustrated in FIG. 14.

Figure 14:
FIG. 14 is a graph illustrating impedance spectra of paired electrodes with dry electrode adhesives having different degree of OH functionality.

FIG. 14 shows the impedance curves of the adhesives described above. The general trend is that the impedance curves shift to lower values for higher OH content indicating an improved suitability to ECG application.

The invention claimed is:

1. An ionically conductive pressure sensitive adhesive composition comprising:
   a) a (meth)acrylate resin present in an amount of 15 to 75% by weight of total weight of the composition; and content of said (meth)acrylate monomer comprising OH-group in said (meth)acrylate resin is at least 20% and no more than 60% by weight of the total weight of the (meth)acrylate resin;
   b) an ionic liquid present in an amount of 0.1 to 35% by weight of the total weight of the composition; and wherein said composition further comprises
   c) an ionic conductivity promoter, different from the ionic liquid, present in an amount of from 0.1 to 25% by weight of the total weight of the composition and comprising one or more choline salts;

d) electrically conductive particles;
   e) polyethylene glycol having a weight average molecular weight of from 300 to 1000 g/mol; and
   f) a solvent selected from the group consisting of ethyl acetate, butyl acetate, ethylene glycol, propylene glycol and mixtures thereof.

2. The ionically conductive pressure sensitive adhesive composition according to claim 1, wherein the ionic liquid is selected from the group consisting of imidazolium acetates, imidazolium sulfonates, imidazolium chlorides, imidazolium sulphates, imidazolium phosphates, imidazolium thiocyanates, imidazolium dicyanamides, imidazolium benzoates, imidazolium triflates, choline triflates, choline saccharinate, choline sulfamates, pyridinium acetates, pyridinium sulfonates, pyridinium chlorides, pyridinium sulphates, pyridinium phosphates, pyridinium thiocyanates, pyridinium dicyanamides, pyridinium benzoates, pyridinium triflates, pyrrolidinium acetates, pyrrolidinium sulfonates, pyrrolidinium chlorides, pyrrolidinium sulphates, pyrrolidinium phosphates, pyrrolidinium thiocyanates, pyrrolidinium dicyanamides, pyrrolidinium benzoates, pyrrolidinium triflates, phosphonium acetates, phosphonium sulfonates, phosphonium chlorides, phosphonium sulphates, phosphonium phosphates, phosphonium thiocyanates, phosphonium dicyanamides, phosphonium benzoates, phosphonium triflates, sulfonium acetates, sulfonium sulfonates, sulfonium chlorides, sulfonium sulphates, sulfonium phosphates, sulfonium thiocyanates, sulfonium dicyanamides, sulfonium benzoates, sulfonium triflates, ammonium acetates, ammonium sulfonates, ammonium chlorides, ammonium sulphates, ammonium phosphates, ammonium thiocyanates, ammonium dicyanamides, ammonium benzoates, ammonium triflates and mixtures thereof.

3. The ionically conductive pressure sensitive adhesive composition according to claim 2, wherein the (meth)acrylate monomer comprising OH-group in said (meth)acrylate resin is present in an amount of at least 22.5% but no more than 60% by weight of the total weight of the (meth)acrylate resin.

4. The ionically conductive pressure sensitive adhesive composition according to claim 1, wherein said (meth) acrylate resin is formed from monomers selected from the group consisting of hydroxyethyl acrylate, hydroxypropyl acrylate, hydroxybutyl acrylate, methyl methacrylate, butyl acrylate, ethylhexylacrylate, acrylic acid, C1-C18 alkyl (meth)acrylate, (meth)acrylamide, vinyl acetate, N-vinyl caprolactam, acrylonitrile, vinyl ether, benzyl (meth)acrylate, cyclohexyl (meth)acrylate, glycidyl (meth)acrylate and mixtures thereof.

5. The ionically conductive pressure sensitive adhesive composition according to claim 1, wherein said (meth) acrylate resin is present in an amount of from 15 to 70% by weight of total weight of the composition.

6. The ionically conductive pressure sensitive adhesive composition according to claim 1, wherein said ionic liquid is selected from the group consisting of 1-ethyl-3-methylimidazolium acetate, 1-ethyl-3-methylimidazolium methanesulfonate, 1-ethyl-3-methylimidazolium trifluoromethanesulfonate, 1-ethyl-3-methylimidazolium chloride, 1-ethyl-3-methylimidazolium ethyl sulphate, 1-ethyl-3-methylimidazolium diethylphosphate, 1-ethyl-3-methylimidazolium thiocyanate, 1-ethyl-3-methylimidazolium dicyanamide, 1-ethyl-3-methylimidazolium benzoate, choline trifluoromethanesulfonate, choline saccharinate, choline acesulfamate, choline N-cyclohexylsulfamate, tris(2-hydroxyethyl)methylammonium methyl sulphate, 1-ethyl-3- methylimidazolium tetrafluoroborate, 1-allyl-3-ethylimidazolium bis(trifluoromethylsulfonyl)imide, choline acetate and mixtures thereof.

7. The ionically conductive pressure sensitive adhesive composition according to claim 1, wherein said ionic liquid is present in an amount of from 0.5 to 35% by weight of total weight of the composition.

8. The ionically conductive pressure sensitive adhesive composition according to claim 1, wherein the ionic conductivity promoter is selected from the group consisting of choline chloride, choline bitartrate, choline dihydrogen citrate, choline phosphate, choline gluconate, choline fumarate, choline carbonate, choline pyrophosphate and mixtures thereof.

9. The ionically conductive pressure sensitive adhesive composition according to claim 8, wherein said ionic conductivity promoter is present in an amount of 0.5 to 35% by weight of the total weight of the composition.

10. The ionically conductive pressure sensitive adhesive composition according to claim 1, comprising the electrically conductive particles in an amount of 0.1 to 35% by weight of the total weight of the composition.

11. The ionically conductive pressure sensitive adhesive composition according to claim 1, wherein the polyethylene glycol has a weight averaged molecular weight of from about 350 to about 750 g/mol.

12. The ionically conductive pressure sensitive adhesive composition according to claim 1, wherein the solvent is present in an amount of from 10 to 90% by weight of the total weight of the composition.

13. The ionically conductive pressure sensitive adhesive composition according to claim 1, wherein said adhesive has an impedance value below 1,000,000 Ohm at 1000 Hz, wherein said impedance is measured by connecting two electrodes coated each with 25 μm of an ionic conductive pressure sensitive adhesive having a contact area of 0.25 cm$^2$.

14. The ionically conductive pressure sensitive adhesive composition according to claim 1, wherein the (meth)acrylate resin is formed from monomers selected from the group consisting of hydroxyethyl acrylate, methyl (meth)acrylate, butyl acrylate, ethylhexylacrylate and mixtures.

15. The ionically conductive pressure sensitive adhesive composition according to claim 14, wherein the (meth) acrylate monomer comprising OH-group in said (meth) acrylate resin is present in an amount of at least 25%, and no more than 55% of the total weight of the (meth)acrylate resin.

16. The ionically conductive pressure sensitive adhesive composition according to claim 15, wherein said ionic liquid is selected from the group consisting of 1-ethyl-3-methylimidazolium benzoate, 1-ethyl-3-methylimidazolium tetrafluoroborate, 1-ethyl-3-methylimidazolium methanesulfonate, 1-ethyl-3-methylimidazolium chloride, 1-ethyl-3-methylimidazolium trifluoromethanesulfonate, choline trifluoromethanesulfonate, 1-ethyl-3-methylimidazolium acetate, choline acetate, 1-ethyl-3-methylimidazolium diethylphosphate, 1-allyl-3-methylimidazolium bis(trifluoromethylsulfonyl)imide, 1-ethyl-3-methylimidazolium ethyl sulphate, 1-ethyl-3-methylimidazolium thiocyanate, 1-ethyl-3-methylimidazolium dicyanamide, choline saccharinate, choline acesulfamate, and mixtures thereof and said ionic liquid is present in an amount of 0.5 to 25% by weight of the total weight of the composition.

17. An electrode for measuring bio-signals from skin comprising the ionically conductive pressure sensitive adhesive composition according to claim 13 for application to skin as a contact medium of the electrode.

18. A dry film of the ionically conductive pressure sensitive adhesive composition according to claim 1.

19. A method of measuring bio-signals from skin comprising steps of: applying an electrode to the skin, said electrode comprising the ionically conductive pressure sensitive adhesive composition according to claim 1 as a contact medium of said electrode; and measuring bio-signals conducted from the skin to the electrode.

* * * * *